US010966769B2

(12) United States Patent
Larsson et al.

(10) Patent No.: US 10,966,769 B2
(45) Date of Patent: Apr. 6, 2021

(54) MIXING AND DISPENSING GUN (71) Applicant: STENHUS I LUND AB, Lund (SE)

(72) Inventors: Ulf Larsson, Malmö (SE); Sten Drennow, Lund (SE)

(73) Assignee: STENHUS I LUND AB, Lund (SE)

( * ) Notice: Subject to any disclaimer, the term of this patent is extended or adjusted under 35 U.S.C. 154(b) by 641 days.

(21) Appl. No.: 15/576,655

(22) PCT Filed: May 25, 2016

(86) PCT No.: PCT/EP2016/061845
§ 371 (c)(1),
(2) Date: Nov. 22, 2017

(87) PCT Pub. No.: WO2016/189057
PCT Pub. Date: Dec. 1, 2016

(65) Prior Publication Data
US 2018/0125557 A1 May 10, 2018

(30) Foreign Application Priority Data
May 25, 2015 (SE) .................................... 1550672-8

(51) Int. Cl.
*A61B 17/88* (2006.01)
(52) U.S. Cl.
CPC ...... *A61B 17/8819* (2013.01); *A61B 17/8822* (2013.01); *A61B 17/8825* (2013.01); *A61B 2017/8838* (2013.01)
(58) Field of Classification Search
CPC ............ A61B 17/8819; A61B 17/8822; A61B 17/8825; A61B 2017/8838
See application file for complete search history.

(56) References Cited

U.S. PATENT DOCUMENTS 3,894,663 A * 7/1975 Carhart ............... B05C 17/0126
222/309
4,425,121 A * 1/1984 Young ..................... A61D 7/00
604/209
(Continued)

FOREIGN PATENT DOCUMENTS

CN 1950041 A 4/2007
CN 102256691 A 11/2011
(Continued)

OTHER PUBLICATIONS

International Search Report and Written Opinion for PCT/EP2016/061845 dated Sep. 9, 2016.

*Primary Examiner* — Anu Ramana
(74) *Attorney, Agent, or Firm* — Merchant & Gould P.C.

(57) ABSTRACT

A device for mixing and dispensing a paste, such as bone cement, comprises a housing (H) with a feeding mechanism (53), and a cylinder (51) for mixing a powder component and a liquid component forming the paste. A piston assembly includes a paste feeding member (57) located in the cylinder, and a tubular member (54). A mixing member (55) is located in the cylinder (51), and a mixing rod (52) extends within the tubular member (54) of the piston assembly. The mixing rod (52) is movable in the tubular member (54) of the piston assembly. The tubular member (54) is provided with external engagement means (T) by which the paste feeding member (57) is movable within the cylinder (51) in a feeding direction. The feeding movement is operated by the feeding mechanism.

13 Claims, 10 Drawing Sheets

(56) References Cited

U.S. PATENT DOCUMENTS

| | | | | |
|---|---|---|---|---|
| 4,546,767 A * | 10/1985 | Smith | ................ | A61B 17/8811 604/224 |
| 4,994,065 A * | 2/1991 | Gibbs | ................ | A61B 17/8822 222/391 |
| 5,842,786 A * | 12/1998 | Solomon | ............. | B01F 11/0054 366/139 |
| 5,893,488 A * | 4/1999 | Hoag | ................ | A61B 17/8822 222/327 |
| 6,386,401 B1 * | 5/2002 | Dodd | ...................... | B05C 17/01 222/391 |
| 6,439,439 B1 | 8/2002 | Rickard et al. | | |
| 7,513,679 B2 * | 4/2009 | Grebius | ............. | A61B 17/8825 366/189 |
| 7,677,418 B2 * | 3/2010 | Henniges | ........... | A61B 17/8827 222/327 |
| 8,372,035 B2 | 2/2013 | Matusch | | |
| 8,845,647 B2 * | 9/2014 | Grebius | ............. | B01F 13/0023 606/94 |
| 9,950,855 B1 * | 4/2018 | Holland | ............ | A61M 5/31501 |
| 2002/0092871 A1 * | 7/2002 | Rickard | ............. | A61B 17/8822 222/327 |
| 2004/0122359 A1 | 6/2004 | Wenz et al. | | |
| 2007/0073424 A1 | 3/2007 | Westerkull | | |
| 2010/0106090 A1 | 4/2010 | Mausch | | |
| 2011/0270260 A1 | 11/2011 | Grebius | | |
| 2013/0090661 A1 | 4/2013 | Henniges et al. | | |

FOREIGN PATENT DOCUMENTS

| | | |
|---|---|---|
| DE | 10252027 A1 | 7/2003 |
| JP | 2003-534061 A | 2/2003 |
| JP | 2007-504923 A | 3/2007 |
| JP | 2010-534092 A | 11/2010 |
| RU | 2363411 C1 | 10/2009 |
| WO | 01/89613 A1 | 11/2001 |
| WO | 0193787 A2 | 12/2001 |
| WO | 2005084591 A1 | 9/2005 |
| WO | 2010054085 A2 | 5/2010 |
| WO | WO 2014/202350 A1 | 12/2014 |

* cited by examiner

MIXING AND DISPENSING GUN

This application is a National Stage Application of PCT/EP2016/061845, filed 25 May 2016, which claims benefit of Swedish Patent Application No. 1550672-8, filed 25 May 2015, which applications are incorporated herein by reference. To the extent appropriate, a claim of priority is made to each of the above disclosed applications.

TECHNICAL FIELD

The present invention relates to a device for mixing, dispensing and applying a paste, such as bone cement.

BACKGROUND

In general terms, bone cement is used for instance in connection with surgery like replacement of hip joints and spinal disc enhancements. When applying the bone cement e.g. to the hip, it is crucial that the injection instrument is sterile. Otherwise the patient runs the risk of getting bacteria into the body, and in a worst case scenario the bacteria is multi-resistant. On a personal level, the recovery time for the patient may increase as well as be more painful. Besides the patient may be forced to further surgery, and in the worse case scenario he/she may even decease. From the society's point of view this kind of mistake in the treatment is very expensive.

Examples of equipment used in practice are the devices for mixing and dispensing bone cement paste described in U.S. Pat. No. 7,513,679B2 and U.S. Pat. No. 8,845,647B2. Devices of this kind, also referred to as mixing guns, comprise a handle assembly with a trigger mechanism by means of which the paste is fed out of a cylinder attached to the handle assembly.

Before dispensing, a liquid (monomer) and bone powder are mixed within the cylinder by means of mixing means which are reciprocated therein. The paste mixing and feeding mechanism includes a rod and spring members of metal, whereas the rest of the device is of plastic.

In U.S. Pat. No. 4,994,065A another injection gun for injecting low volume, high pressure shots of bone cement is disclosed. The injection gun comprises a rod provided with notches extending through a tube. The notches interact with pawls in a trigger assembly. The feeding mechanism requires several parts: two sets of pivot pins, springs, and pawls as well as a compression spring. The multitude of parts provides the injector with a large amount of possible error sources.

A device for controlling the injection of bone cement into a cavity is described in U.S. Pat. No. 4,546,767A. This device comprises a ratchet rod provided with notches on its underside, which interacts with a ratchet trigger, together affecting a plunger for feeding of cement.

A further injection gun for injecting high-viscosity masses into the human body is described in WO2014/202350. This gun comprises a cylinder and a mixing assembly operated by a rod which is axially movable. Furthermore, the gun has a feeding assembly including a threaded rod which upon turning (by a handle) pushes the material within the cylinder. The mixing and the injection of the bone cement are performed in two separate steps. The injection of the bone cement is performed by using two hands, where one hand holds the gun and the other hand is used for turning the handle. This procedure thus involves several steps which take up valuable time in the stressful environment in which the operation is performed.

As to further background art, the mixing and injection guns known from U.S. Pat. No. 6,439,439B1 and DE10252027A1 should be mentioned.

Surgery, such as hip joints replacement, is conducted in stressful environments under high time pressure. Long patient waiting lists force the surgeons to be time efficient in order to manage a plurality of patients each day. It is crucial that the bone cement has the right viscosity when applied to the human body, and the time frame from mixing to applying is thus very short. Furthermore, due to the complex injection guns existing on the market a surgery is performed by at least three persons; a surgeon, a nurse and/or an assisting nurse or doctor. From the above it is understood that there is room for improvements.

SUMMARY

An object of the present invention is to provide a new type of mixing and dispensing device which is improved over prior art and which eliminates or at least mitigates the drawbacks discussed above. More specifically, an object of the invention is to provide a paste mixing and dispensing device which is cost-efficient compared to existing dispensers, which is less prone to chip formation and which is easier to sterilize. These objects are achieved by a device set forth in the appended claim 1 with preferred embodiments defined in the dependent claims related thereto.

An idea of the general inventive concept is to design the new device by a limited number of components consisting of a material or of materials which meet today's demands as regards single use equipment and which are suitable for disposable handling. Single use equipment has the benefit of not creating wear products which may come in contact with the blood and tissue of the patient during surgery. Furthermore, single use equipment is less heavy which reduces the risk of repetitive stain injuries of the surgeon.

In an aspect of the invention, there is provided a device for mixing and dispensing a paste, such as bone cement, said device comprising a housing with a feeding mechanism; a cylinder for mixing a powder component and a liquid component forming the paste, said cylinder being connected to said housing; a piston assembly comprising a paste feeding member located in the cylinder and a tubular member; a mixing assembly comprising a mixing member located in the cylinder and a mixing rod which extends within said tubular member of the piston assembly, said mixing rod being movable in the tubular member of the piston assembly; wherein said tubular member of the piston assembly is provided with external engagement means by which said paste feeding member is movable within the cylinder in a feeding direction, said feeding movement being operated by the feeding mechanism.

The device may further comprise an actuator assembly which is accommodated in the housing and which in a first position is in engagement with the external engagement means of the tubular member, and which in a second position is disengaged from the engagement means for stepwise movement of the tubular member, in order to move the paste feeding member in the feeding direction. This provides the effect that the device is very easy to operate since the user operating steps are reduced by that the mixing and feeding mechanism cooperate with each other.

Preferably, the actuator assembly is configured to switch between its first and second position—engaged or disengaged from said engagement means, said actuator assembly being operated by a trigger included in the feeding mechanism.

The actuator assembly may comprise a link system including at least one pivot attached to the housing and one pivot point attached to the actuator assembly.

In one embodiment, the trigger is connected to a resilient return member which is biasing the trigger in such way, that one trigger strike corresponds to a predetermined stepwise movement of the tubular member of the piston assembly, and thereby corresponding movement of the paste feeding member.

The engagement means of the tubular member may comprise teeth. This allows for stepwise feeding, moving one or a plurality of teeth at a time.

Preferably, the tubular member of the piston assembly extends partly within the housing and partly outside the housing.

In one embodiment, the tubular member of the piston assembly is provided with a security latch which prevents movement of the paste feeding member in a direction opposite to the feeding direction.

The security latch may be an annular member which is slipped onto the tubular member of the piston assembly.

Preferably, at least the housing and the cylinder as well as all components of the mixing and feeding mechanisms are made of plastics material. Since the components making up the single-use type guns are made of plastics material, it makes them suitable for disposal.

The stepwise movement of the tubular member may be asymmetrical. Having asymmetrical feeding allows for an almost step-free feeding of the tubular member.

In one embodiment, asymmetrical stepwise movement of the tubular member is achieved by the tubular member having external engagement means arranged on two sides, a upper side and a lower side, wherein the external engagement means on the upper side is arranged with an axial offset in relation to the external engagement means of the lower side. The device thus allows for a very accurate and precise feeding of the paste into the human body.

The actuator assembly may comprise a stop mechanism to prevent the paste feeding member to move in a direction opposite the feeding direction. This provides the safety that the device could not be reused.

Preferably, the actuator assembly comprises snap means configured to interact with the tubular member using snap engagement. Using the snap means, the stepwise feeding of the tubular member can thus be controlled in a desirable manner.

The actuator assembly may further comprises spring elements which permits reciprocal gripping and releasing of the tubular member so as to stepwise feed the paste out from the cylinder.

The mixing and dispensing device as discussed above further has the benefit of being very easy to operate. The operating steps are reduced in that the mixing and feeding mechanism cooperate with each other.

The manufacturing process of the new device is cheaper and has an easier assembly process.

Further features and advantages of the invention and its embodiments will appear from the appended claims as well as the detailed description.

BRIEF DESCRIPTION OF THE DRAWINGS

Embodiments of the invention will be described in the following; references being made to the appended diagrammatical drawings which illustrate non-limiting examples of how the inventive concept can be reduced into practice.

FIGS. 3-12 illustrate how a device according to still another embodiment is loaded and operated in preparation for use.

DETAILED DESCRIPTION

Hereinafter, certain embodiments will be described more fully with reference to the accompanying drawings. The invention may, however, be embodied in many different forms and should not be construed as limited to the embodiments set forth herein; rather, these embodiments are provided by way of example so that this disclosure will be thorough and complete, and will fully convey the scope of the invention, such as it is defined in the appended claims, to those skilled in the art.

Figure 1:
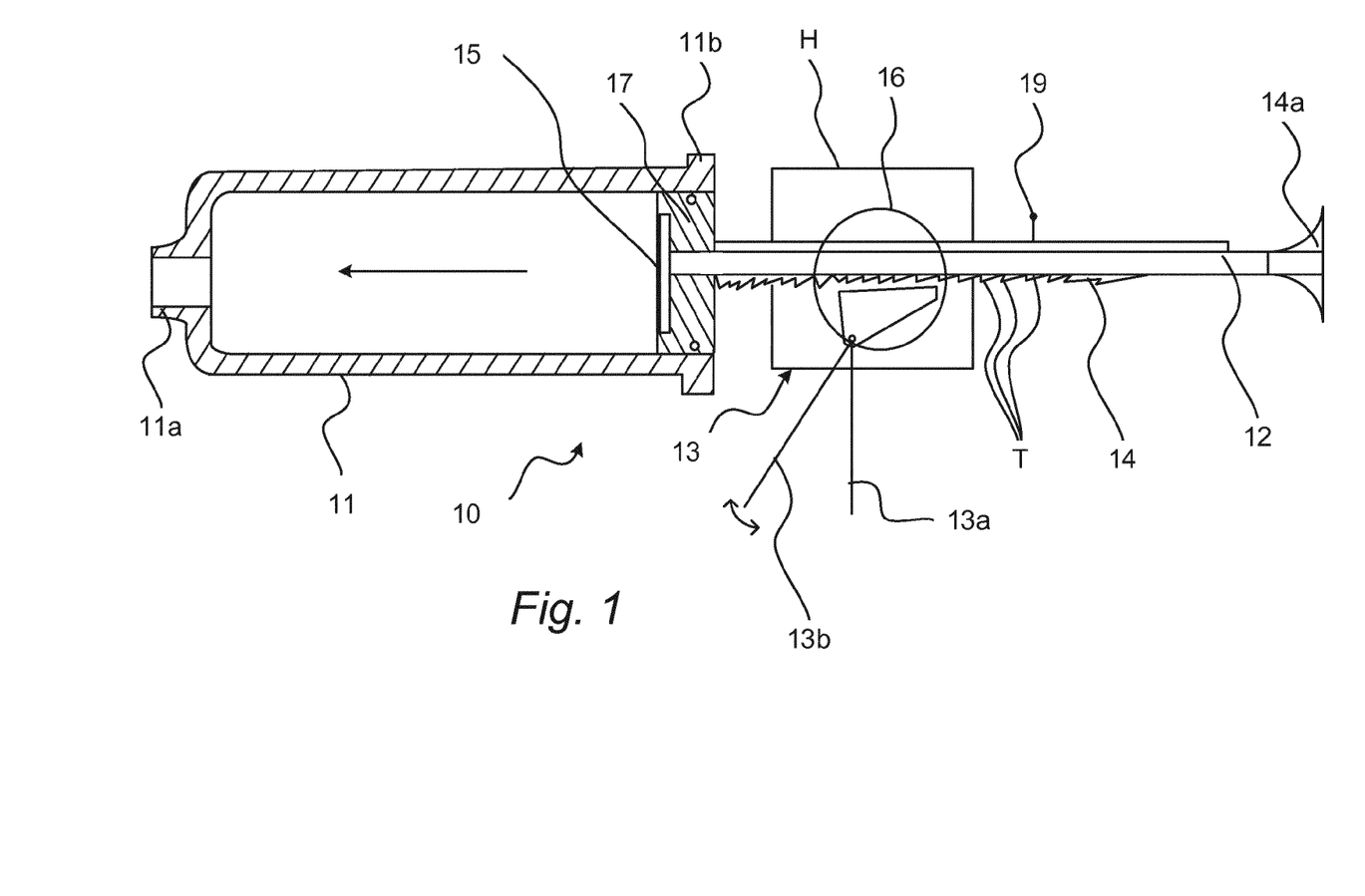
FIG. 1 is an axial section of a device according to an embodiment.

In FIG. 1 there is shown a device 10 according to a basic-version embodiment. The mixing and dispending device or gun 10 comprises a housing H, and a cylinder 11 configured to contain a bone powder component (such as for example bone cement powder) and a liquid component (monomer) which when mixed form the paste, such as bone cement. The cylinder 11 has an opening 11a through which the paste is dispensed, and an attachment element or portion 11b for attaching the cylinder 11 to housing H having a feeding mechanism 13.

The feeding mechanism 13 comprises a fixed handle 13a and a trigger handle 13b which is movable between an outer and an inner position. The paste feeding process is operated by the handle/trigger assembly 13a, 13b. The feeding mechanism 13 further comprises an actuator assembly or member 16 which allows for an adjustable feeding of the paste.

The device 10 includes an elongate tubular portion or member 14 at least partially located in the cylinder 11 and a mixing element or assembly comprising a mixing member 15 and an elongate mixing rod 12.

The tubular elongate member 14 is provided with engagement means or teeth T allowing a piston or paste feeding member 17 to be stepwise moved in a feeding direction (as indicated in the figure). The tubular member 14 is arranged so that it is axially stepwise movable inside the cylinder 11. The mixing element or member 15 is arranged in the cylinder 11 and the mixing member 15 is connected to the mixing rod 12 which is mounted freely slidable or movable in the tubular elongate member 14. The mixing rod 12 is axially displaceable. Mixing of the liquid and the powder within the cylinder 11 is accomplished by a reciprocal movement of the mixing rod 12, so that the mixing member 15 is moved within the cylinder 11.

The tubular member 14 and the mixing rod 12 may be constructed as two pieces being fixedly connected during assembly or constructed as a single part. The paste feeding member 17 and the tubular elongate member 14 form together a piston assembly. A mixing handle 14a is attached to the end of the mixing rod 12 or at the end of the tubular member 14. Preferably, the handle 14a is detachable.

Once the mixing of the bone powder component and the liquid component (monomer) is completed and a paste P is formed, the paste P is dispensed through the opening 11a of the cylinder 11. The paste P is pressed out from the cylinder 11 by an assembly created by the mixing member 15 and the paste feeding member 17. This assembly of the mixing member 15 and the paste feeding member 17 presses the paste P out of the cylinder 11 by use of a feeding mechanism 33. This is further shown in FIG. 12.

Figure 2:
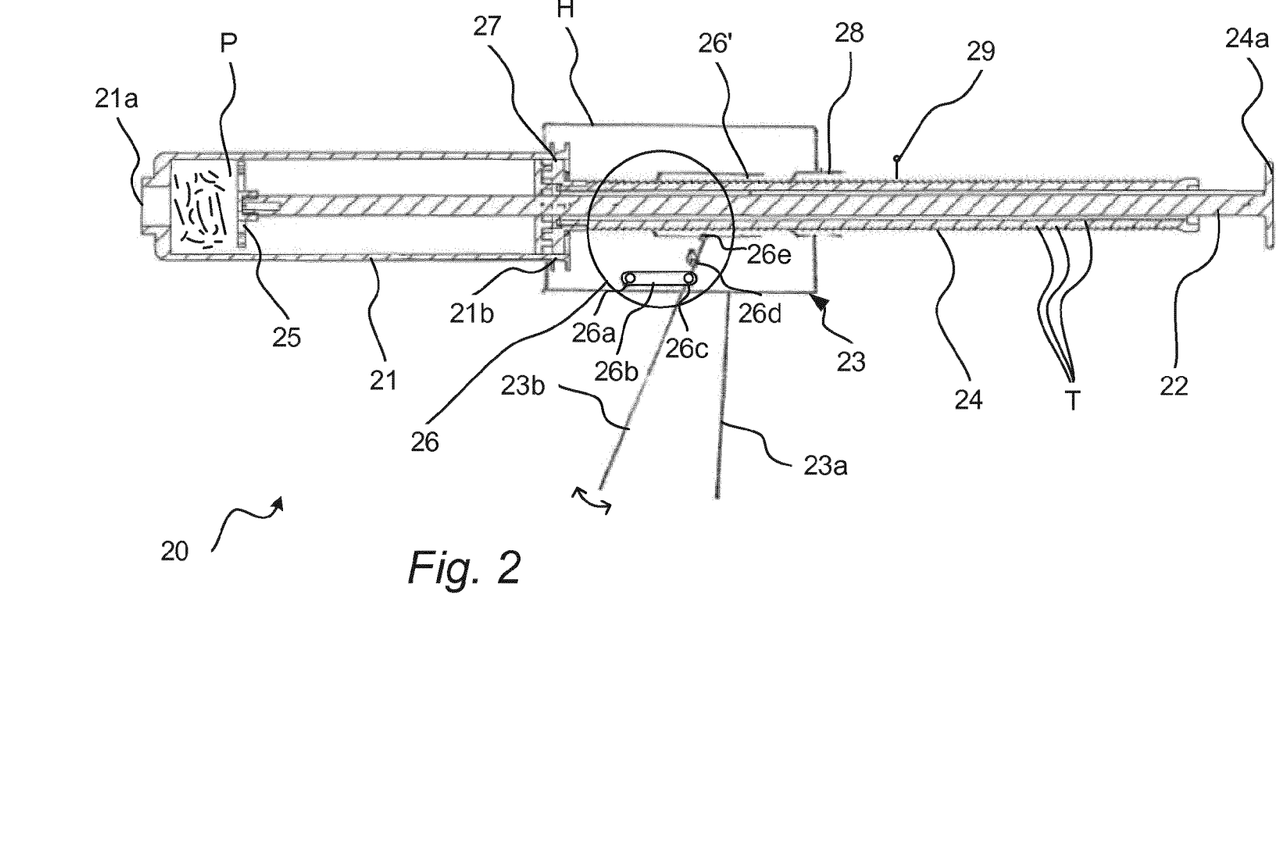
FIG. 2 is an axial section of a device according to a further embodiment.
Figure 3:
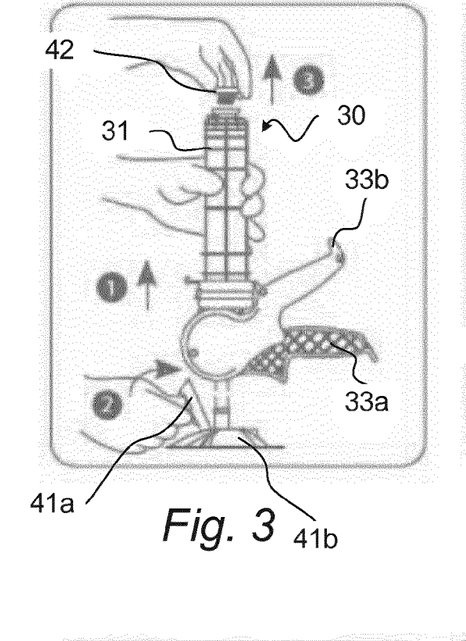
FIG. 3 is a side view of a device according to an embodiment, which is prepared for loading.
Figure 4:
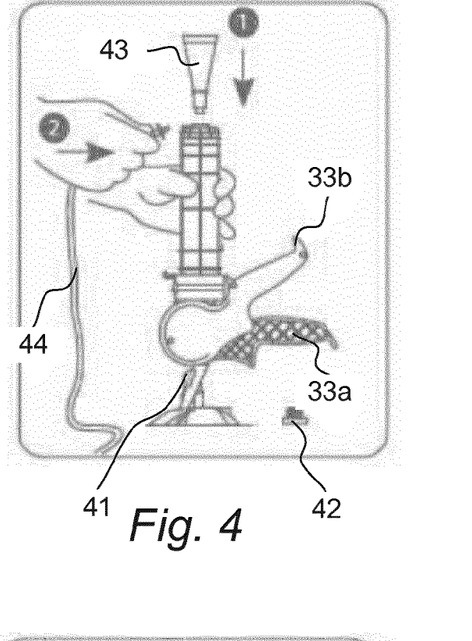
FIG. 4 shows the device of FIG. 3 being connected to a vacuum source and provided with a funnel.
Figure 5:
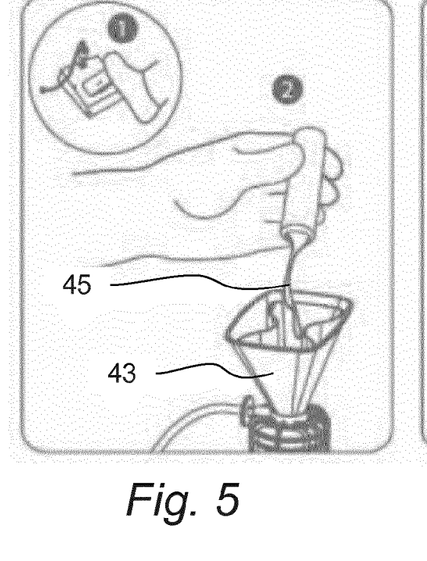
FIG. 5 shows the device of FIG. 4 being filled with a liquid component.
Figure 6:
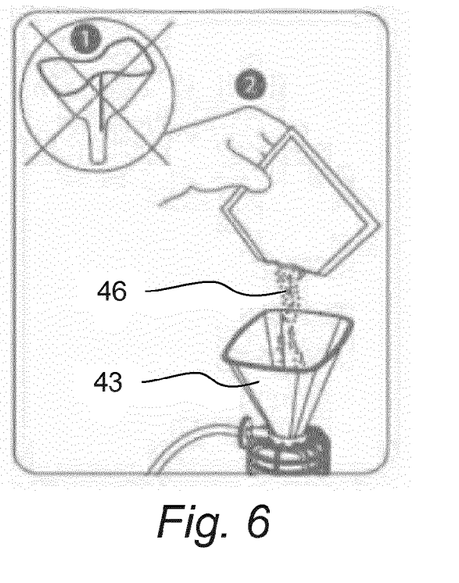
FIG. 6 shows the device of FIG. 5 being filled with a powder component.

In FIG. 2 there is illustrated a device 20 according to further developed embodiment. Hence, the device 20 comprises a cylinder 21 with an opening 21a and an attachment element or portion 21b. The device 20 further comprises a tubular portion or member 24 and a mixing element or assembly comprising a mixing member 25 and a mixing rod 22 located in the cylinder 21. The mixing rod 22 is mounted so that it is axially displaceable in the cylinder 21, and the tubular member 24 is arranged so that it is axially stepwise movable inside the cylinder 21. A mixing handle 24a is attached to one end of the mixing rod 22 to facilitate the use of the mixing step. These components are similar to the corresponding components of the device 10 shown in FIG. 1.

The feeding mechanism 23 comprises an actuator assembly 26 which interacts with the gripping means T on the tubular member 24, such that an adjustable feeding of the paste is accomplished during the feeding mode (not shown in FIG. 2). In FIG. 2 this adjustable feeding is achieved by snap engagement between a member 26' and external gripping means T, such as teeth, on the tubular member 24. In this embodiment, the teeth T are circumferential around the tubular member 24.

The member 26' is actuated by the trigger 23b via a link/pivot system. The trigger 23b is biased in a direction away from the handle 23a by means of a return spring means between a pin 26a attached to the housing H and a first attachment point 26c on the trigger 23b. In the embodiment, the return spring action is accomplished by means of an elastic rubber ring 26b between the pin 26a and the first attachment point 26c. The upper end of the trigger 23b is attached to the member 26' at a second attachment point 26e. The link/pivot system further has pivot point 26d.

In one embodiment, the trigger 23b is connected to a resilient return member 26b which is biasing the trigger 23b in such way, that one trigger strike corresponds to a predetermined stepwise movement of the tubular member 24 of the piston assembly, and thereby corresponding movement of the paste feeding member 27.

Furthermore, the device 20 comprises a security latch 29 which prevents the device 20 to be used unintentional. When the latch 29 is removed it is possible to—by pushing the trigger handle 23b—feed the paste out of the cylinder 21. A stop mechanism 28 is provided in the housing of the feeding mechanism 23 and controls the movement of the paste feeding member 27. The stop mechanism may be an annular member 28.

The stepwise feeding of the tubular member 24 operated by the feeding mechanism 23 can be controlled in a desirable manner. For instance, a full strike of the trigger 23b may correspond to a two-teeth movement of the tubular member 24 whereas a half strike of the trigger 23b may correspond to a one-tooth movement. Of course, other set ups are possible. It is an advantage for the user to be able to apply different stepwise movements. By the arrangement discussed above, the user applies the small-step feeding movement in the position where the trigger 23b is close to the stationary part 23a of the handle. The stepwise feeding will be further described in conjunction to FIGS. 15a-d.

The handling of a device 30, which is basically of the above described type, is schematically illustrated in FIGS. 3-12. The device 30 comprises a cylinder 31 with an opening 31a and an attachment element 31b. Further, the device 30 comprises a tubular member 34 and a mixing element or assembly including a mixing member and a mixing rod located in the cylinder 31. The feeding mechanism 33 comprises a fixed handle 33a and a trigger handle 33b which is movable between an outer and an inner position. These components are similar to the corresponding components of the device 10 and 20 shown in FIGS. 1 and 2.

Figure 7:
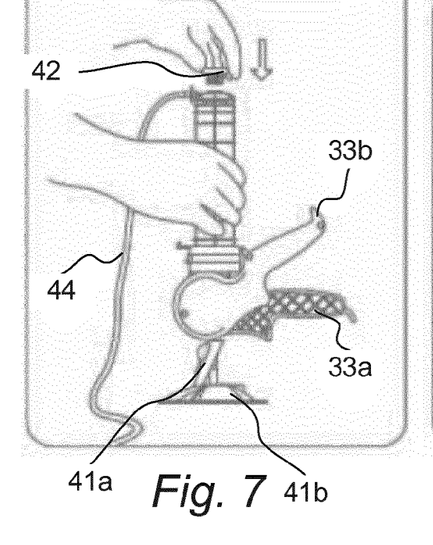
FIG. 7 shows the device of FIG. 6 being prepared for a mixing step.
Figure 8:
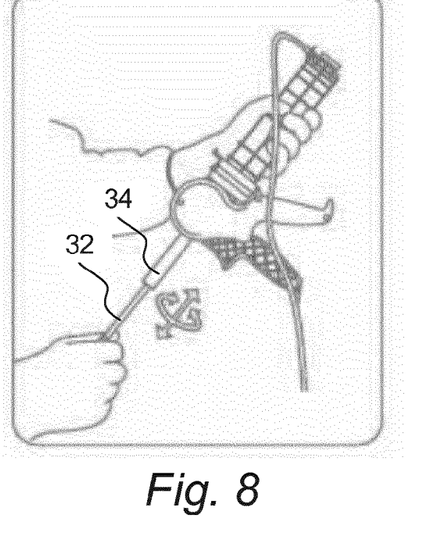
FIG. 8 shows the device of FIG. 7 during mixing of the liquid and powder components.
Figure 9:
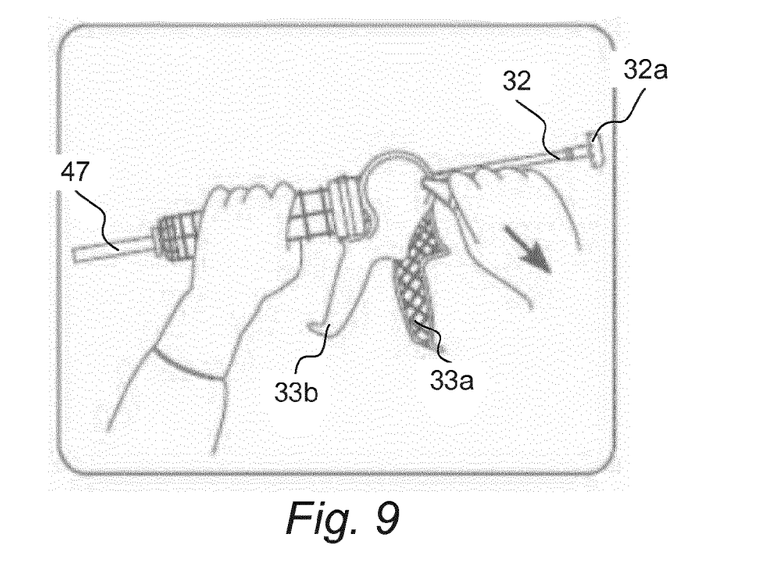
FIG. 9 shows the device of FIG. 8 being unlatched.
Figure 10:
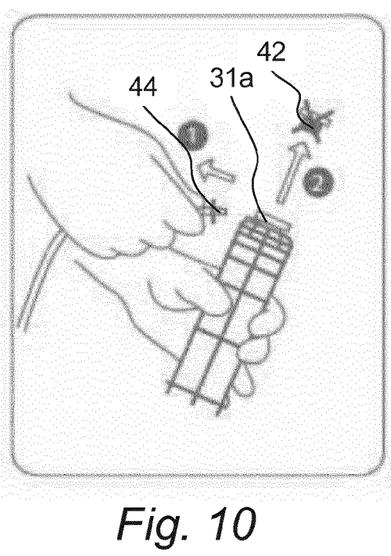
FIG. 10 shows the device of FIG. 9 being disconnected from vacuum.
Figure 11:
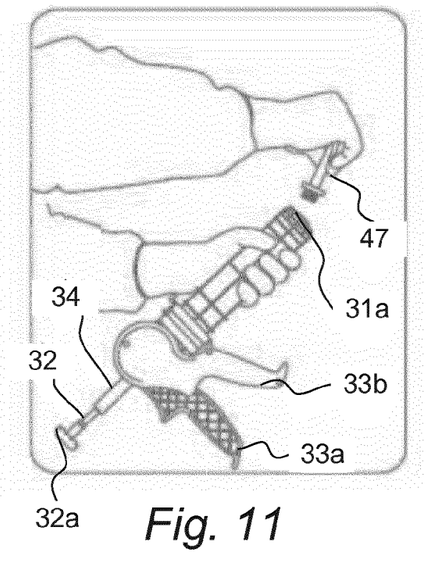
FIG. 11 shows the device of FIG. 10 being provided with an output pipe.
Figure 12:
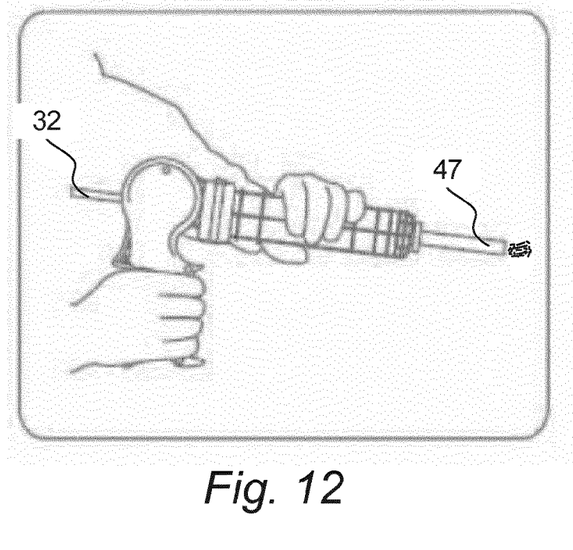
FIG. 12 shows the device of FIG. 11 being prepared for use.

As can be seen in FIGS. 3-12, the device 30 is placed on a base 41b and a spacer 41a is arranged to keep the mixing assembly at a distance from the cylinder opening 31a so as to ease the filling of the bone powder 46 and the liquid 45, such as monomer. A plug 42 is detached from the opening of the cylinder 31 so that a funnel 43 may be placed on the cylinder opening 31a such that paste can be refilled. Furthermore, a hose 44 is attached to the cylinder 31. The hose 44 may apply a negative pressure or a vacuum, hence a pressure difference is achieved. The liquid 45 and the powder 46 are transferred through the funnel 43 and the plug 41 is attached again, as shown in FIG. 7. In FIG. 8, the mixing rod 32 is rotated in different directions so as to mix the bone powder 46 and the liquid 45 so as to form bone cement. When fully mixed (see FIGS. 9 and 10), the security latch and the hose 44 are removed. FIGS. 11 and 12 shows a discharge means in the form of a dispensing tube 47 that is attached to the outlet of the cylinder 31a instead of the plug 41. The device 30 is now ready to be used by the surgeon. The surgeon uses the feeding mechanism 33 so as to feed out bone cement out from the opening in the cylinder 31a and the dispensing tube 47 into the human body.

It should be noted that the steps shown in FIGS. 9 and 10 can be switched.

Figure 13:
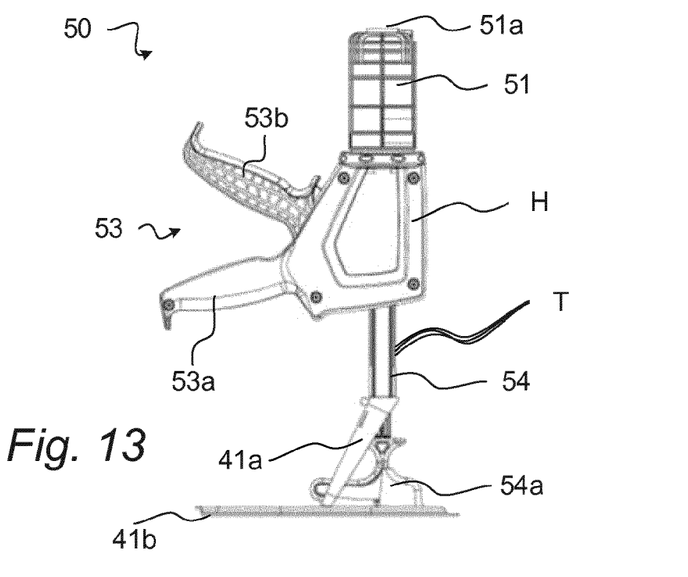
FIG. 13 is a side view of a device according to a further embodiment, being in its loading position.
Figure 14:
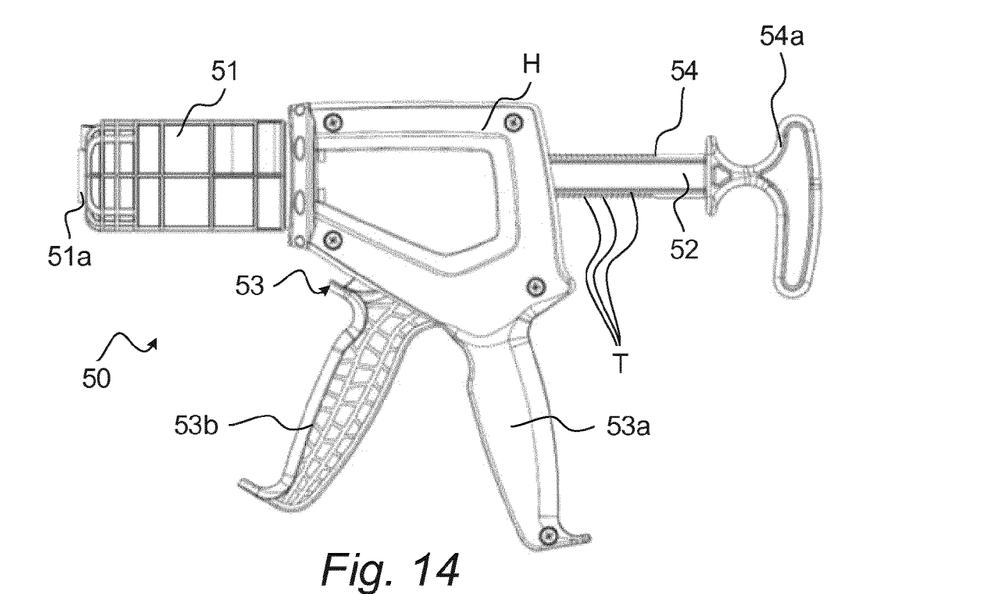
FIG. 14 is a side view of the device of FIG. 13 ready to use.
Figure 15:
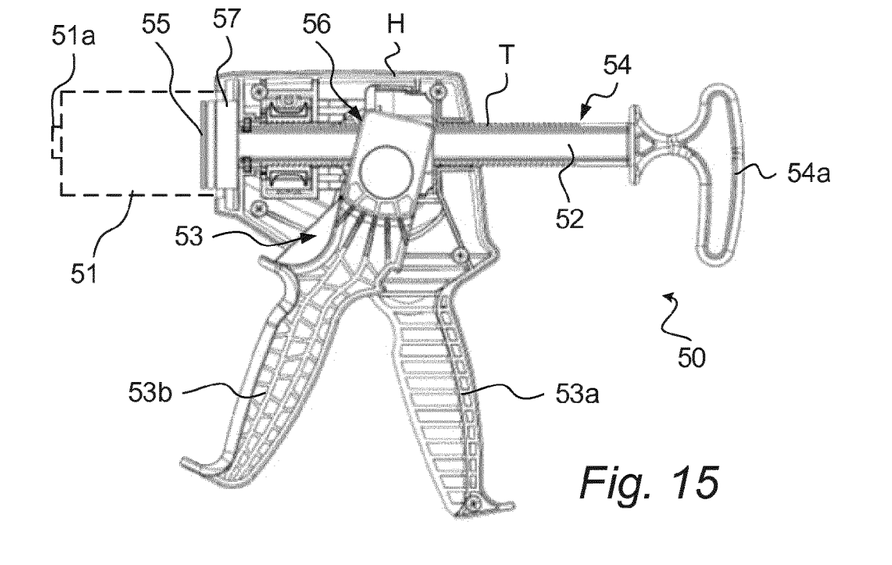
FIG. 15 is a section showing the interior mechanism of the device of FIGS. 13-14.

In FIGS. 13-15 there is illustrated a mixing and dispensing device or gun 50 according to further developed embodiment. This device 50 comprises a housing H and a cylinder 51 which has an opening 51a through which bone cement paste is dispensed. A tubular member 54 is arranged at least partially in the cylinder 51. The cylinder 51 is connected to a feeding mechanism 53 which is arranged to feed out the paste from the cylinder 51.

The feeding mechanism 53 comprises a fixed handle 53a, a trigger handle 53b and an actuator assembly 56 which allows for an adjustable feeding of the paste. Furthermore, the device 50 comprises a mixing assembly comprising a mixing member 55 and an elongate mixing rod 52. The mixing rod 52 is axially displaceable in the cylinder 51 and the tubular member 54 is arranged so that it is axially stepwise movable inside the cylinder 21. Further, the device 50 comprises a mixing handle 54a, the mixing handle 54a may be arranged at one end of the mixing rod 52.

The device 50 in FIG. 13 is shown in a position placed on a base 41b arranged with a spacer 41a so as to keep the mixing assembly at a distance from the cylinder opening 51a so as to ease the filling of the bone powder and the liquid.

During mixing, the liquid and bone powder are mixed into bone cement by rotating the mixing rod 52 so that the mixing member 55 is rotated inside the cylinder 51. When the device is in a mixing mode, the mixing member 55 is arranged freely from the paste feeding member 57. The mixing step is further shown in FIG. 8 where one can see that the user rotates the mixing rod 52 to mix the paste together. During the step of mixing, the mixing rod 52 can be moved both in the feeding direction and in a direction opposite the feeding.

Once the mixing of the bone powder component and the liquid component (monomer) is completed and a paste is formed, the paste is ready to be dispensed through the opening 51a in the cylinder 51. The paste is pressed out from the device 50 by an assembly created by the mixing member 55 and the paste feeding member 57. Hence, in the feeding mode, the mixing member 55 is arranged in conjunction to the paste feeding member 57. By using the feeding mechanism 53, such as pressing the trigger handle 53b towards the fixed handle 53a, the paste feeding member 27 (and thus the mixing member 55 being arranged thereon) presses the paste out from the cylinder 51. This is further shown in FIG. 12.

Although not shown in FIGS. 13-15, the device 50 further comprises a security latch (referred to as 29 in FIG. 2) which prevents the device 50 to be used unintentional. When the latch is removed it is possible to feed the paste out of the cylinder 51.

The device 50 being in a feeding step is shown in FIGS. 15-18. During feeding, the actuator assembly 56 is actuated by the trigger 53b via a link/pivot system. The trigger 53b is biased in a direction away from the handle 53a by means of a resilient return member 56b (shown in FIG. 19) arranged between a pin and a first attachment point. The link/pivot system further has pivot point 56d (shown in FIG. 18).

In the embodiment shown, the tubular member 54 has a substantially rectangular cross-sectional shape, having a first side 54b and second opposite side 54c provided with external gripping means T such as teeth. In an alternative embodiment, the teeth T are circumferential around the tubular member 54 (not shown).

Figure 16:
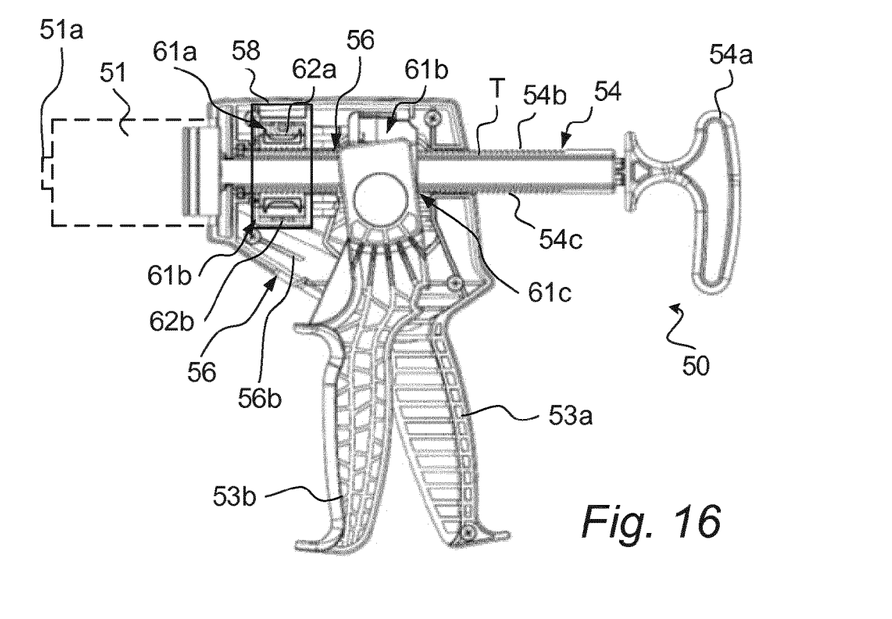
FIG. 16 is a section showing an initial feeding position.
Figure 17:
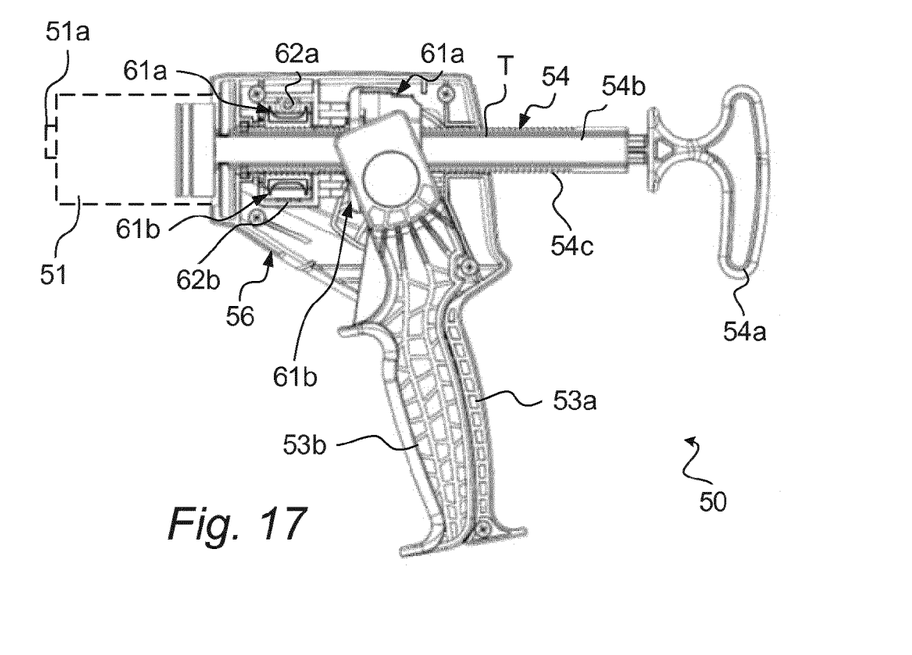
FIG. 17 is a section showing another feeding position.
Figure 18:
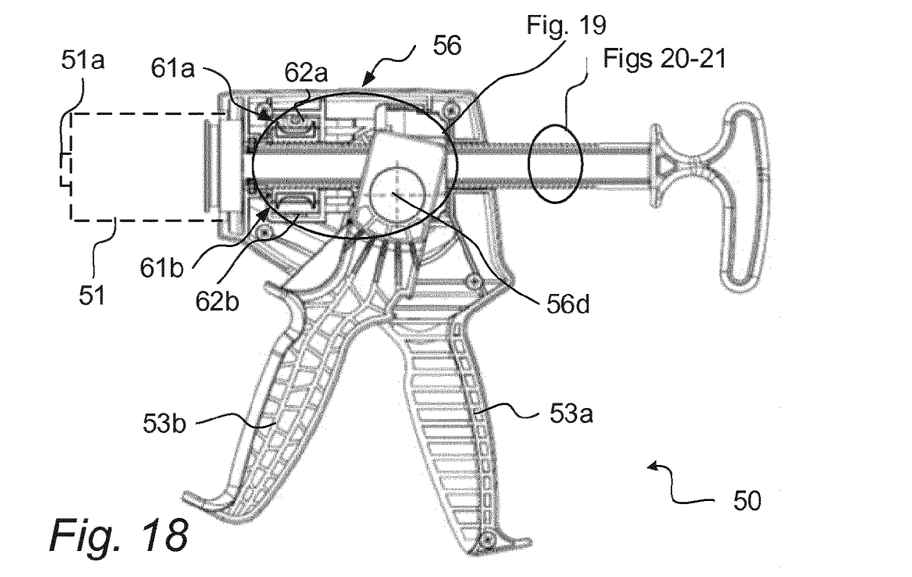
FIG. 18 is a section showing a pivot point.

As seen in FIG. 16 (and which is even more clearly illustrated in FIG. 19), the actuator assembly 56 comprises two pairs of snap means 61a-d, where each pair is arranged on two sides of the tubular member 54. The snap means 61a-d has gripping means, such as teeth, which are arranged to interact, using snap engagement, with the external gripping means T on the tubular member 54. In that way the actuator assembly 56 interacts with the tubular member 54 using snap engagement.

Each snap means 61a-d comprises a spring element 62a-d, which may be a rubber ring or another type of resilient return member. The spring elements 62a-d permit reciprocal gripping and releasing of the tubular member 54 so as to stepwise feed the paste out from the device 50. The movement of the spring elements 62a-d is indicated by arrows in FIG. 19.

Figure 19:
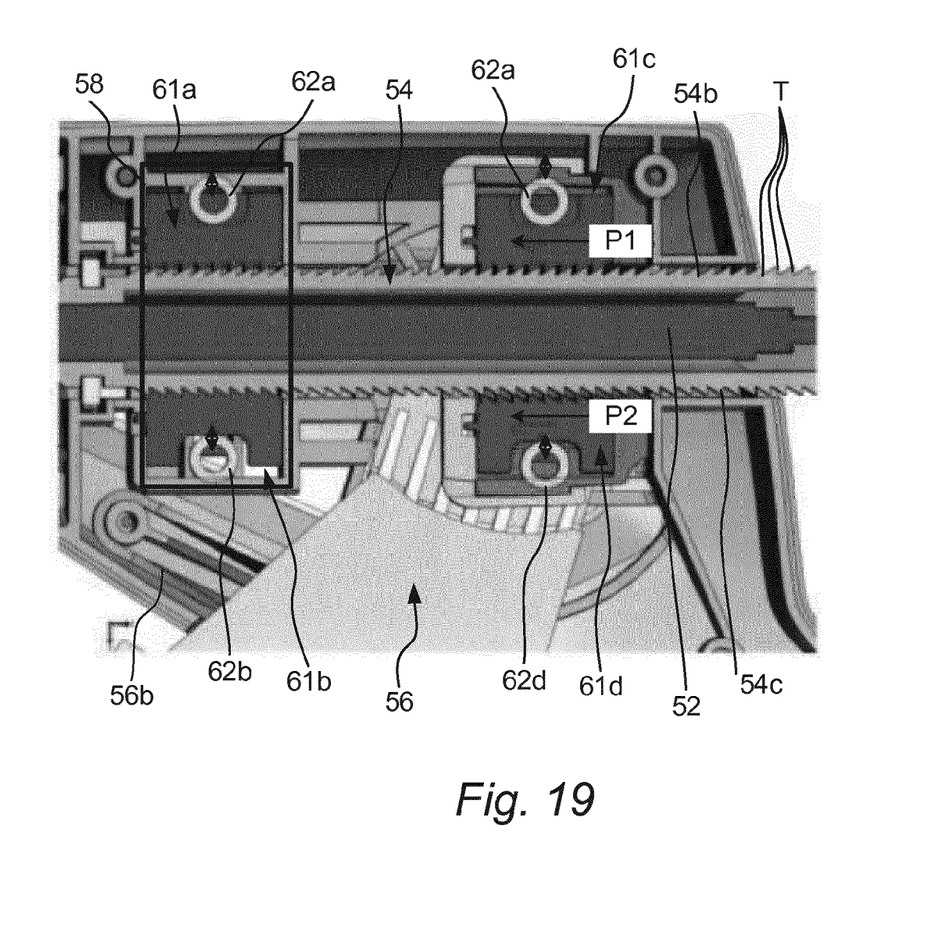
FIG. 19 is a partial enlarged section of the actuator assembly of the device shown in FIGS. 13-18.

In the embodiment shown in FIGS. 15-19, one pair of snap means 61a-b acts as a stop mechanism 58 (marked as a box in FIG. 19 for the convenience of the reader). In the embodiment shown, the stop mechanism 58 is arranged closer to the paste feeding member 57 than the other pair of snap means 61c-d. The stop mechanism 58 controls the movement of the paste feeding member 57. The paste feeding member 57 is only allowed to be moved in the paste feeding direction. Hence, the device 50 is thus not configured to be reused. However, it should be noted that in the mixing step, when the user manually moves the mixing rod 52 (and not the tubular member 54), there is no restriction in moving the rod 52 both in the feeding direction and in a direction opposite the feeding direction.

Using the snap means 61a-b, the axially stepwise feeding of the tubular member 54, operated by the feeding mechanism 53, can thus be controlled in a desirable manner. By slightly pressing the handle 53b of the feeding mechanism 53 the snap means 61c-d are moved one step, i.e. one tooth, in the feeding direction. This is indicated by arrows P1, P2 in FIG. 19.

Figure 20:
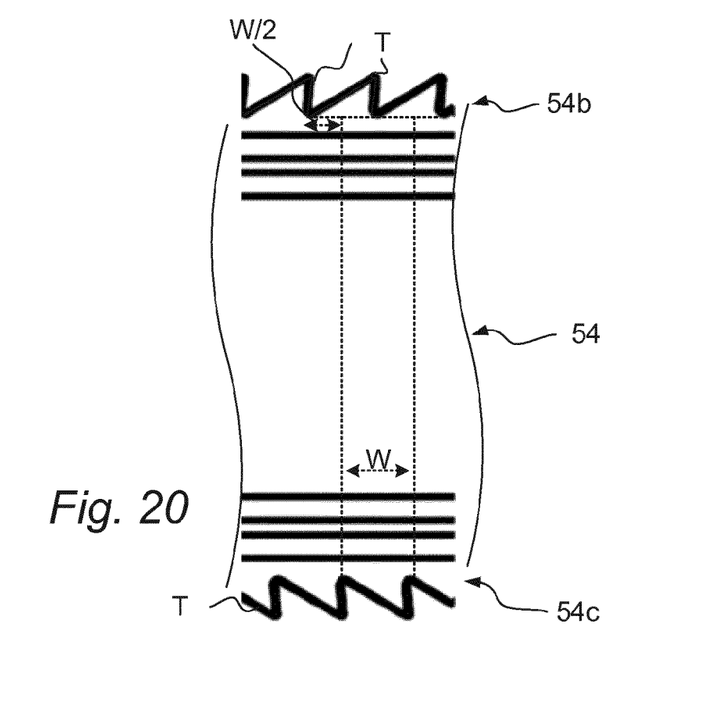
FIG. 20 is a partial enlarged section of the tubular member of the device shown in FIGS. 13-18.
Figure 21:
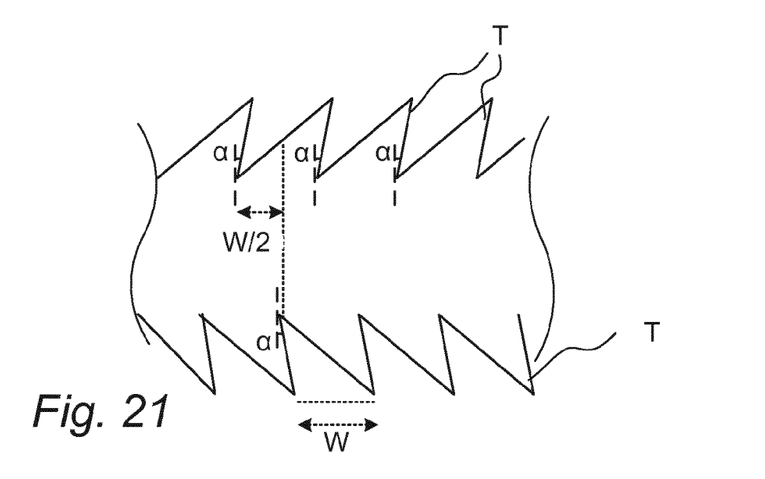
FIG. 21 is a partial enlarged section of the tubular member of the device shown in FIGS. 13-18.

In one embodiment shown in FIGS. 20-21, the stepwise feeding is asymmetrical. Asymmetrical feeding is achieved by having a tubular member 54 provided with one set of teeth arranged on a first side 54b and another set of teeth arranged on a second opposite side 54c of the tubular member 54. The set of teeth arranged on the first side 54b of the tubular member 54 is arranged asymmetrical to the second set of teeth arranged on the second opposite side 54c. The axial offset between the two set of teeth may be approximately 50%. Hence, if the distance between to teeth on one side is W, the teeth are axially shifted by a half teeth width, i.e. the distance W/2. In other words, the peaks of the teeth arranged on the first side 54b are axially shifted by a half teeth width compared to the teeth arranged on the second opposite side 54c. This arrangement allows for an almost step-free feeding of the tubular member 54. The device 50 thus allows for a very accurate and precise feeding of the paste into the human body.

As seen in FIG. 21, the teeth T may be inclined an angle α. The angle is preferably between 2° and 10° and more preferred around 5°.

The mixing and dispensing guns described above are thus used in the following manner. First, the gun is loaded with liquid and powder components which are fed into the cylinder. Second, the liquid and power components are mixed into a paste by moving the mixing rod back and forth and/or by rotating the mixing rod to the right and left. After the mixing is completed a paste is formed in the cylinder. The paste is discharged by pressing the fixed handle and the trigger handle, so that a stepwise feeding of the paste is achieved. Once sufficient amount of paste has been discharge the mixing and dispensing gun is thrown away in a recycle bin.

The mixing and dispensing guns described herein are of single-use type. All components making up the guns are made of plastics material, which make them suitable for disposal. Single use equipment has the benefit of not creating wear products which may come in contact with the blood and tissue of the patient during operation. Furthermore, single use equipment is less heavy (up to half the weight from a conventional reusable gun) which reduces the risk of repetitive stain injuries of the surgeon.

The plastic members of the mixing and dispensing device are injection molded plastic members. In one embodiment, the plastic material is a biocompatible polymer. Preferably the plastic comprise olefin fibers, polypropylene or polyoxymethylene.

Preferably, the assembly process of the plastic members is taking place in a clean room. The fully assembled product is then finally sterilized using for example ETO.

In an aspect of the invention, there is provided a device for mixing and dispensing a paste, such as bone cement, comprising a housing with a feeding mechanism, a cylinder for mixing a powder component and a liquid component forming the paste. The cylinder is connected to the housing. Further, the device has a piston assembly with a paste feeding member located in the cylinder, and a tubular portion. A mixing element comprising a mixing member is located in the cylinder, and a mixing rod extends within the tubular portion of the piston assembly. The mixing rod is movable in the tubular portion of the piston assembly. The tubular portion of the piston assembly is provided with external engagement means by which the paste feeding member is movable within the cylinder in a feeding direction the feeding movement being operated by the feeding mechanism.

It should be appreciated that the inventive concept is not limited to the embodiments described herein, and many modifications are feasible within the scope of the invention set forth in the appended claims.

The invention claimed is:

1. A device for mixing and dispensing a bone cement paste formed by a powder component and a liquid component, said device comprising: a housing with a feeding mechanism; a cylinder for mixing said powder component and said liquid component forming said paste, said cylinder being connected to said housing; a piston assembly comprising a paste feeding member which is located in the cylinder, and a tubular member; a mixing assembly comprising a mixing member which is located in said cylinder, and a mixing rod which extends within said tubular member of the piston assembly, said mixing rod being movable in said tubular member of the piston assembly; wherein said tubular member of the piston assembly is provided with external engagement means by which said paste feeding member is movable within said cylinder in a feeding direction to provide a feeding movement, said feeding movement being operated by said feeding mechanism.

2. The device as claimed in claim 1, further comprising an actuator assembly which is accommodated in said housing and which in a first position is in engagement with said external engagement means of the tubular member, and which in a second position is disengaged from said engagement means for stepwise movement of said tubular member, in order to move said paste feeding member in said feeding direction.

3. The device as claimed in claim 2, wherein said stepwise movement of the tubular member is an asymmetrical stepwise movement, wherein said asymmetrical stepwise movement of the tubular member is achieved by said tubular member having external engagement means arranged on two sides, namely a first side and a second opposite side, wherein said external engagement means on said first side is provided with an axial offset in relation to said external engagement means of said second side.

4. The device as claimed in claim 2, wherein said actuator assembly comprises a stop mechanism to prevent said paste feeding member to move in a direction opposite said feeding direction.

5. The device as claimed in claim 2, wherein said actuator assembly comprises snap means configured to interact with said tubular member using snap engagement.

6. The device as claimed in claim 5, wherein said actuator assembly further comprises spring means permitting reciprocal gripping and releasing of said tubular member so as to stepwise feed said paste out from said cylinder.

7. The device as claimed in claim 2, wherein said actuator assembly is configured to switch between its first and second position engaged or disengaged from said engagement means, said actuator assembly being operated by a trigger included in said feeding mechanism.

8. The device as claimed in claim 7, wherein said actuator assembly comprises a link system including at least one pivot attached to said housing and one pivot attached to said actuator assembly.

9. The device as claimed in claim 7, wherein said trigger is connected to a resilient return member which is biasing the trigger in such way, that one trigger strike corresponds to a predetermined stepwise movement of said tubular member of the piston assembly, and thereby corresponding movement of said paste feeding member.

10. The device as claimed in claim 1, wherein said engagement means of said tubular member comprise teeth.

11. The device as claimed in claim 1, wherein said tubular member of the piston assembly extends partly within the housing and partly outside the housing.

12. The device as claimed in claim 1, wherein said tubular member of the piston assembly is provided with a security latch which is configured to prevent movement of said paste feeding member in a direction opposite to said feeding direction.

13. The device as claimed in claim 1, wherein at least said housing and said cylinder as well as all components of said mixing and feeding mechanisms are made of plastic.

* * * * *